US012661260B2

(12) United States Patent
Brown et al.

(10) Patent No.: US 12,661,260 B2
(45) Date of Patent: Jun. 23, 2026

(54) DEVICES AND METHODS FOR ILLUMINATING AN INTRAOCULAR IMPLANT

(71) Applicants: RHB Research, LLC, Atlanta, GA (US); Georgia Tech Research Corporation, Atlanta, GA (US)

(72) Inventors: Reay H. Brown, Atlanta, GA (US); Jun Ueda, Atlanta, GA (US)

(73) Assignees: RHB Research, LLC, Atlanta, GA (US); Georgia Tech Research Corporation, Atlanta, GA (US)

( * ) Notice: Subject to any disclaimer, the term of this patent is extended or adjusted under 35 U.S.C. 154(b) by 1214 days.

(21) Appl. No.: 16/966,945

(22) PCT Filed: Feb. 4, 2019

(86) PCT No.: PCT/US2019/016460
§ 371 (c)(1),
(2) Date: Aug. 3, 2020

(87) PCT Pub. No.: WO2019/152905
PCT Pub. Date: Aug. 8, 2019

(65) Prior Publication Data
US 2021/0045917 A1 Feb. 18, 2021

Related U.S. Application Data

(60) Provisional application No. 62/628,095, filed on Feb. 8, 2018, provisional application No. 62/625,601, filed on Feb. 2, 2018.

(51) Int. Cl.
*A61F 9/00* (2006.01)
*A61B 90/30* (2016.01)
(Continued)

(52) U.S. Cl.
CPC ............ *A61F 9/0017* (2013.01); *A61B 90/30* (2016.02); *A61F 9/00781* (2013.01); *A61F 9/009* (2013.01); *A61B 2090/306* (2016.02)

(58) Field of Classification Search
CPC ............... A61B 90/30; A61B 2090/306; A61F 9/00781; A61F 9/0017; A61F 9/0008;
(Continued)

(56) References Cited

U.S. PATENT DOCUMENTS 5,558,669 A 9/1996 Reynard
8,007,459 B2 8/2011 Haffner et al.
(Continued)

FOREIGN PATENT DOCUMENTS

WO 2017/108498 A1 6/2017

OTHER PUBLICATIONS

PCT International Search Report and Written Opinion for PCT Application No. PCT/US2019/016460 mailed May 6, 2019 (8 pages).

*Primary Examiner* — Thomas McEvoy
(74) *Attorney, Agent, or Firm* — Eversheds-Sutherland (US) LLP

(57) ABSTRACT

Embodiments of the present disclosure provide a delivery device for implanting an intraocular stent. In one embodiment, the delivery device may include a guide and a fiber optic cable. The guide may be configured to receive at least a portion of the intraocular stent thereon. The fiber optic cable may engage the guide and be configured to receive at least a portion of the intraocular stent thereon. The guide may have an elongated shape defining a first longitudinal axis, the fiber optic cable may have an elongated shape defining a second longitudinal axis, and the first longitudinal axis may be coaxial with the second longitudinal axis.

11 Claims, 9 Drawing Sheets

(51) Int. Cl.
    *A61F 9/007*        (2006.01)
    *A61F 9/009*        (2006.01)

(58) Field of Classification Search
    CPC ........ A61F 9/00; A61F 9/007; A61F 9/00736;
                A61F 9/00763; A61F 9/00754; A61F
                9/00745; A61F 9/009; A61F 2/95–97
    See application file for complete search history.

(56)                     References Cited

U.S. PATENT DOCUMENTS

| | | | |
|---|---|---|---|
| 2004/0102729 A1* | 5/2004 | Haffner ............... | A61F 9/00781 623/1.11 |
| 2005/0171507 A1 | 8/2005 | Christian et al. | |
| 2006/0149194 A1 | 7/2006 | Conston et al. | |
| 2016/0135992 A1 | 5/2016 | Schaller et al. | |
| 2016/0151151 A1* | 6/2016 | Kleinman ................. | A61F 2/14 623/6.12 |

* cited by examiner

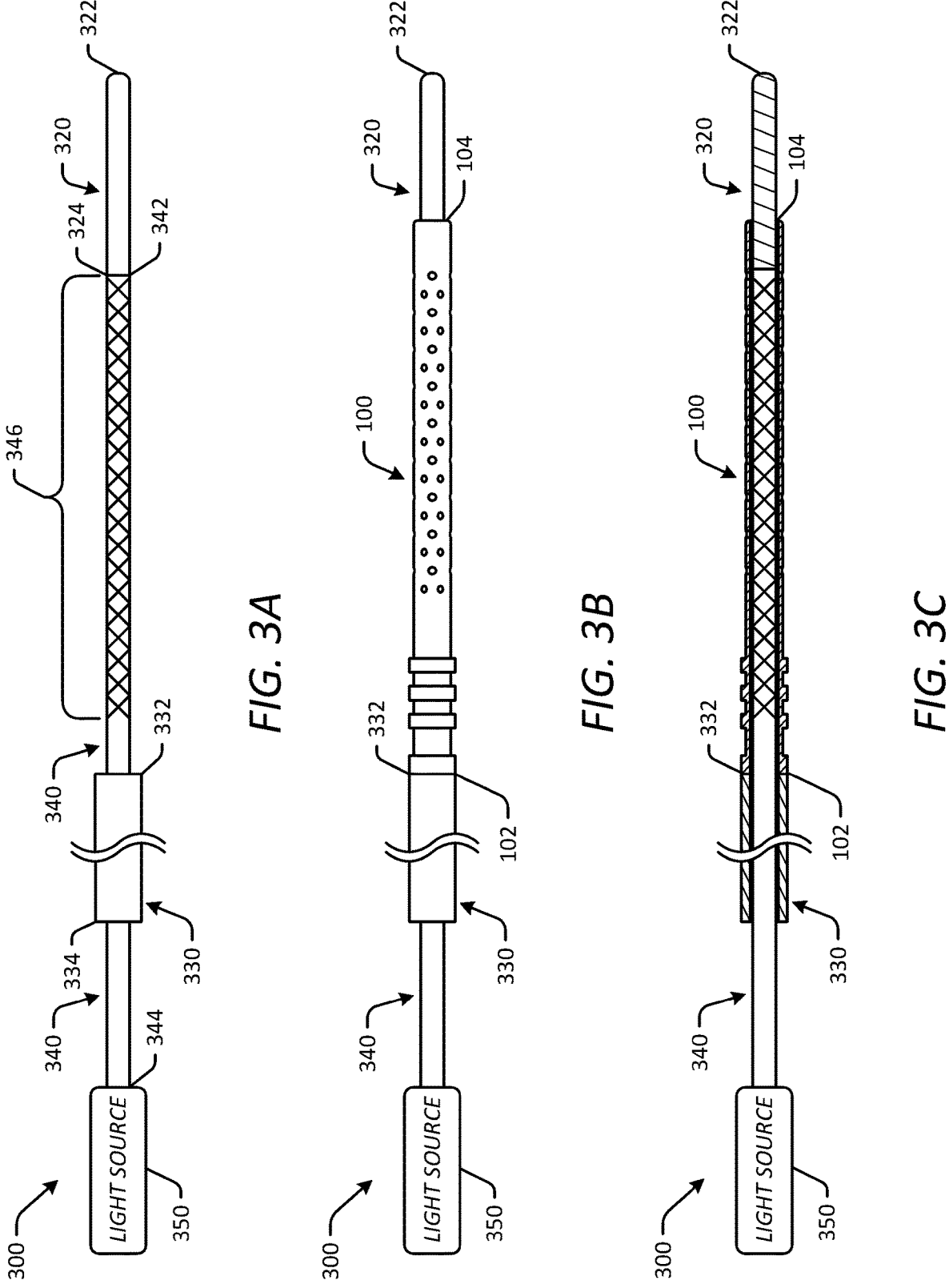

DEVICES AND METHODS FOR ILLUMINATING AN INTRAOCULAR IMPLANT

CROSS REFERENCE TO RELATED APPLICATIONS

This application claims the priority benefit of PCT/US2019/016460 filed on Feb. 4, 2019 which claims the priority benefit to U.S. Provisional Patent Application Nos. 62/625,601 and 62/628,095, filed Feb. 2, 2018 and Feb. 8, 2018, respectively, which applications are incorporated herein by reference.

FIELD OF THE DISCLOSURE

The present disclosure relates generally to intraocular implants and more particularly to devices and methods for illuminating an intraocular stent to facilitate visualization and positioning of the stent within the eye during implantation.

BACKGROUND OF THE DISCLOSURE

Various types of intraocular devices may be implanted within a patient's eye for treatment of different eye disorders, such as glaucoma. For example, an intraocular stent may be used to treat open-angle glaucoma by implanting the stent such that aqueous humor flows from the anterior chamber of the eye through the stent. In this manner, the aqueous outflow from the anterior chamber may lower intraocular pressure. In some instances, the stent may be implanted to provide fluid communication between the anterior chamber and the suprachoroidal space of the eye, such that the pressure gradient drives aqueous humor from the anterior chamber into the suprachoroidal space. Although this approach may provide effective and sustained lowering of intraocular pressure, existing techniques for implantation of the stent between the anterior chamber and the suprachoroidal space may present certain drawbacks. For example, surgical gonioscopy generally may be required in order to view the iridocorneal angle and direct the stent to the implantation site, and it may be challenging to maintain focus through the goniolens during implantation. Moreover, visibility of the stent may be limited as the stent is advanced toward and into the implantation site, necessitating highly accurate surgical skills in order to position the stent properly with respect to the anterior chamber and the suprachoroidal space. Finally, when the stent implantation is carried out in combination with cataract surgery, it may be cumbersome and time-consuming for the surgeon to reposition the patient's head, reposition the goniolens, and focus through the goniolens to implant the stent.

Accordingly, there remains a need for improved devices and methods for easily, efficiently, and accurately implanting an intraocular stent within an eye, such as between the anterior chamber and the suprachoroidal space thereof.

SUMMARY OF THE DISCLOSURE

Various embodiments described herein provide devices and methods for implanting an intraocular stent within a patient's eye. As described below, the devices and methods may allow surgeons to easily, efficiently, and accurately implant an intraocular stent in a manner that avoids the above-described challenges associated with existing intraocular stent implantation techniques.

According to one aspect, delivery devices for implanting an intraocular stent are provided. In one embodiment, a delivery device may include a guide and a fiber optic cable. The guide may be configured to receive at least a portion of the intraocular stent thereon. The fiber optic cable may engage the guide and be configured to receive at least a portion of the intraocular stent thereon. The guide may have an elongated shape defining a first longitudinal axis, the fiber optic cable may have an elongated shape defining a second longitudinal axis, and the first longitudinal axis may be coaxial with the second longitudinal axis.

In certain embodiments, at least a portion of the fiber optic cable may be positioned within the guide. In certain embodiments, the guide may include a central bore defined therein, and at least a portion of the fiber optic cable may be positioned within the central bore. In certain embodiments, the guide may further include a plurality of apertures defined therein and extending transverse to the first longitudinal axis. In certain embodiments, the apertures may be formed as through holes extending from an outer circumferential surface of the guide to the central bore. In certain embodiments, the apertures may be formed as blind holes. In certain embodiments, the guide may include a central passage defined therein and open along a portion of a circumference of the guide, and at least a portion of the fiber optic cable may be positioned within the central passage. In certain embodiments, the guide may further include a plurality of apertures defined therein and extending transverse to the first longitudinal axis. In certain embodiments, the apertures may be formed as through holes extending from an outer circumferential surface of the guide to the central passage. In certain embodiments, the apertures may be formed as blind holes.

In certain embodiments, a distal end of the fiber optic cable may abut the guide. In certain embodiments, the fiber optic cable may include a textured surface configured to diffuse light. In certain embodiments, the textured surface may be positioned within the intraocular stent when the at least a portion of the intraocular stent is received on the fiber optic cable. In certain embodiments, the delivery device may further include a tube configured to abut a proximal end of the intraocular stent. The tube may have an elongated shape defining a third longitudinal axis, and the third longitudinal axis may be coaxial with the first longitudinal axis and the second longitudinal axis. In certain embodiments, the guide may be configured to translate relative to the tube. In certain embodiments, the guide and the fiber optic cable may be configured to translate relative to the tube. In certain embodiments, the delivery device may further include a housing, and at least a portion of the guide and at least a portion of the fiber optic cable are positioned within the housing. In certain embodiments, the guide may be configured to translate relative to the housing. In certain embodiments, the guide and the fiber optic cable may be configured to translate relative to the housing. In certain embodiments, the delivery device may further include a light source in communication with the fiber optic cable and configured to generate light for transmission to the fiber optic cable.

In another embodiment, a delivery device may include a guide and a fiber optic cable. The guide may be configured to receive at least a portion of the intraocular stent thereon. The fiber optic cable may engage the guide and be configured to receive at least a portion of the intraocular stent thereon. The guide may have an elongated shape defining a first longitudinal axis, the fiber optic cable may have an elongated shape defining a second longitudinal axis, and the first longitudinal axis may be offset from the second longitudinal axis.

In certain embodiments, at least a portion of the fiber optic cable may be positioned within the guide. In certain embodiments, the guide may include a central passage defined therein and open along a portion of a circumference of the guide, and at least a portion of the fiber optic cable may be positioned within the central passage. In certain embodiments, the guide may further include a plurality of apertures defined therein and extending transverse to the first longitudinal axis. In certain embodiments, the apertures may be formed as through holes extending from an outer circumferential surface of the guide to the central passage.

In still another embodiment, a delivery device may include a guide and a fiber optic tube. The guide may be configured to receive at least a portion of the intraocular stent thereon. The fiber optic tube may engage the guide and be configured to abut an end of the intraocular stent. The guide may have an elongated shape defining a first longitudinal axis, the fiber optic cable may have an elongated shape defining a second longitudinal axis, and the first longitudinal axis may be coaxial with the second longitudinal axis.

In certain embodiments, at least a portion of the guide may be positioned within the fiber optic tube. In certain embodiments, the fiber optic tube may include a tubular casing and one or more fiber optic cables positioned within a wall thickness of the casing and configured to abut the end of the intraocular stent. In certain embodiments, the one or more fiber optic cables may include a circumferential array of fiber optic cables positioned within the wall thickness of the casing. In certain embodiments, each of the one or more fiber optic cables may include a textured surface positioned along a distal end thereof, and the distal end may be configured to abut the end of the intraocular stent.

These and other aspects and embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein:

FIG. 3A is a side view of a portion of a delivery device for implanting an intraocular stent in accordance with one or more embodiments of the disclosure, as may be used with the delivery device of FIG. 2A.

FIG. 3B is a side view of the portion of the delivery device of FIG. 3A, with the intraocular stent of FIG. 1A mounted thereto for implantation.

FIG. 3C is a partial cross-sectional side view of the portion of the delivery device of FIG. 3A and the intraocular stent of FIG. 1A.

DETAILED DESCRIPTION OF THE DISCLOSURE

Various embodiments of the present disclosure provide improved devices and methods for easily, efficiently, and accurately implanting an intraocular stent within a patient's eye. Such devices and methods may address one or more of the above-described problems experienced with existing technology for implanting an intraocular stent within an eye, such as between the anterior chamber and the suprachoroidal space thereof, for treatment of glaucoma. For example, delivery devices described herein may include one or more fiber optic cables configured to illuminate an intraocular stent mounted thereto. In this manner, such delivery devices may provide a surgeon with enhanced visibility of the stent as well as the location of the stent within a patient's eye during an implantation procedure. As a result, the delivery devices and related methods described herein may obviate the need for surgical gonioscopy, allowing the surgeon to directly implant the stent without having to focus through a goniolens throughout the implantation procedure. Ultimately, the devices and methods of the present disclosure may allow the surgeon to easily visualize the stent during implantation and confidently direct the stent to the desired implantation site, while avoiding the cumbersome and time-consuming aspects of existing implantation techniques.

Embodiments of the present disclosure are described herein below with reference to the accompanying drawings, in which some, but not all, embodiments are shown. Indeed, the systems and methods disclosed may be embodied in many different forms and should not be construed as limited to the embodiments set forth herein; rather, these embodiments are provided so that this disclosure is thorough and complete and fully conveys the scope of the systems and methods to those skilled in the art. Like reference numbers refer to like elements throughout. The singular forms "a," "an," and "the" can refer to plural instances unless the context clearly dictates otherwise or unless explicitly stated.

Figures 1A, 1B, 1C:
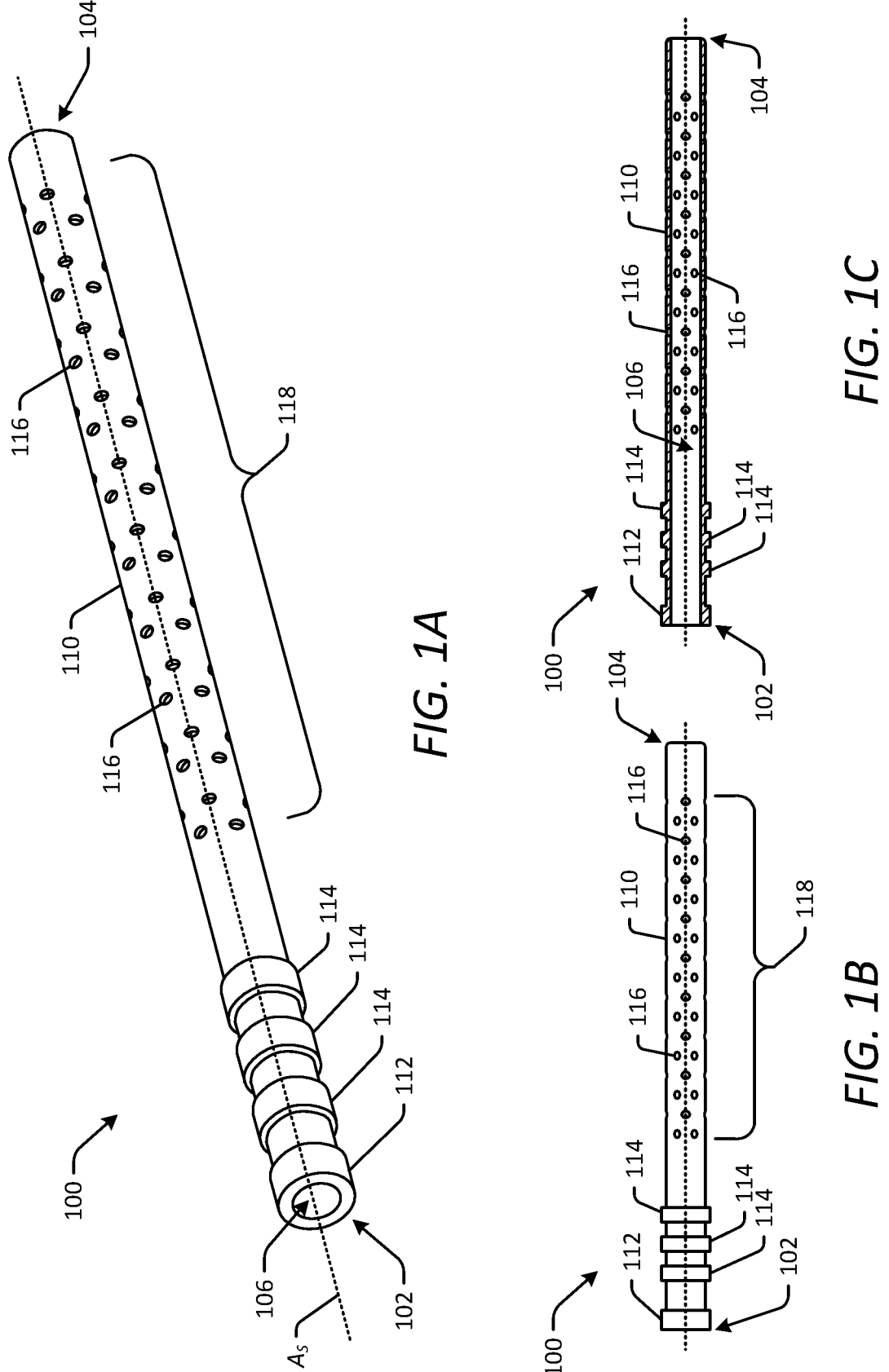
FIG. 1A is a perspective view of an intraocular stent in accordance with one or more embodiments of the disclosure.
FIG. 1B is a side view of the intraocular stent of FIG. 1A.
FIG. 1C is a cross-sectional side view of the intraocular stent of FIG. 1A.
Figure 1D:
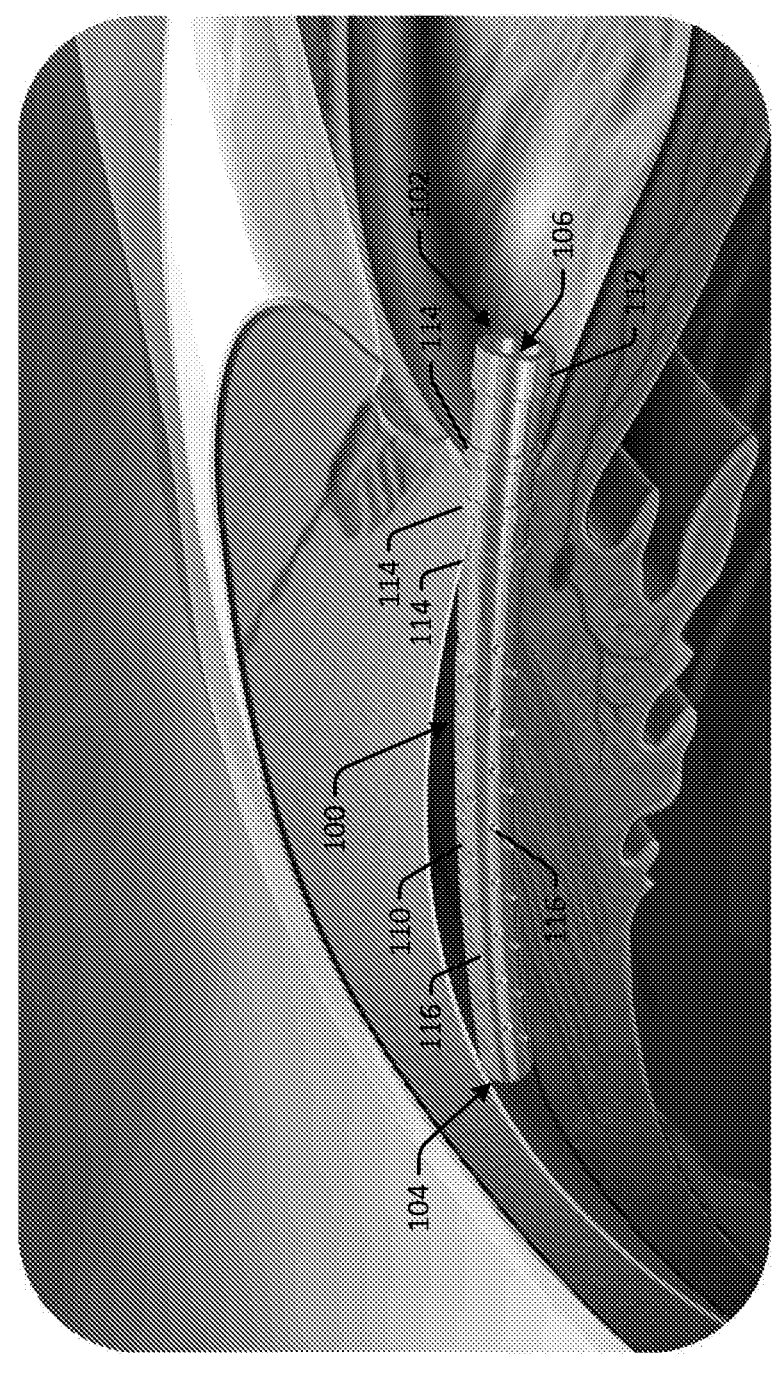
FIG. 1D is a partial cross-sectional perspective view of the intraocular stent of FIG. 1A implanted within an eye.

Referring now to the drawings, FIGS. 1A-1D illustrate an intraocular stent 100 (which also may be referred to herein as an "implantable stent" or simply a "stent") according to one or more embodiments of the disclosure. As described below, the stent 100 may be configured for implantation within the eye of a patient to treat one or more eye disorders, such as glaucoma. For example, the intraocular stent 100 may be used to treat open-angle glaucoma by implanting the stent 100 such that aqueous humor flows from the anterior chamber of the eye through the stent 100. In this manner, the aqueous outflow from the anterior chamber may lower intraocular pressure. In some instances, the stent 100 may be implanted to provide fluid communication between the anterior chamber and the suprachoroidal space of the eye, as shown in FIG. 1D, such that the pressure gradient drives aqueous humor from the anterior chamber into the supra-choroidal space. It will be appreciated, however, that the stent 100 may be used for treatment of other types of eye disorders, and that the stent 100 may be delivered to other implantation sites within the eye to facilitate drainage of aqueous humor or other fluids.

As shown, the intraocular stent 100 may have an elongated shape extending along a longitudinal axis $A_S$ of the stent 100, between a proximal end 102 (which also may be referred to as a "first end") and a distal end 104 (which also may be referred to as a "second end") thereof. The stent 100 may have a generally tubular shape defining a central lumen 106 therethrough. As shown, the central lumen 106 may extend from the proximal end 102 to the distal end 104 of the stent 100. Upon implantation, the central lumen 106 may allow aqueous humor, or other fluids, to flow through the stent 100. In certain embodiments, as shown, the stent 100 may have a circular cross-sectional shape, taken in a direction perpendicular to the longitudinal axis $A_S$ thereof, and the central lumen 106 also may have a circular cross-sectional shape. Other shapes and configurations of the stent 100 may be used.

According to the illustrated embodiment, the intraocular stent 100 may include a tubular body 110, a flange 112, and one or more retention rings 114. The body 110 may extend along the entirety, or at least a majority, of the stent 100 in the direction of the longitudinal axis $A_S$ thereof and may define the central lumen 106 therethrough. The flange 112 may be integrally formed with the body 110 and extend radially outward therefrom. In certain embodiments, as shown, the flange 112 may be positioned at the proximal end 102 of the stent 100. In other embodiments, the flange 112 may be positioned near but spaced apart from the proximal end 102. During implantation of the stent 100, the flange 112 may abut a mating portion of a delivery device, as described below, for driving the stent 100 to a desired implantation site. In certain embodiments, upon implantation of the stent 100, the flange 112 may reside within the anterior chamber of the eye, as shown in FIG. 1D, and may assist in prevent the stent 100 from being over-advanced into the implantation site and/or inhibiting migration of the stent 100 from the implantation site. In certain embodiments, as shown, the flange 112 may have a circular cross-sectional shape, taken in the direction perpendicular to the longitudinal axis $A_S$, although other shapes of the flange 112 may be used.

As shown, the one or more retention rings 114 may be integrally formed with the body 110 and extend radially outward therefrom. Although three (3) retention rings 114 are shown in the illustrated embodiment, any number of retention rings 114 may be used. The retention rings 114 may be positioned near but spaced apart from the proximal end 102 of the stent 100 and the flange 112. Further, the retention rings 114 may be spaced apart from one another in the direction of the longitudinal axis $A_S$. In certain embodiments, upon implantation of the stent 100, one or more of the retention rings 114 may reside within the anterior chamber of the eye, and one or more of the retention rings 114 may reside within the suprachoroidal space, as shown in FIG. 1D. Each retention ring 114 may engage surrounding tissue of the eye, thereby inhibiting migration of the stent 100 from the implantation site. In certain embodiments, as shown, the retention rings 114 each may have a circular cross-sectional shape, taken in the direction perpendicular to the longitudinal axis $A_S$, although other shapes of the retention rings 114 may be used.

In certain embodiments, as shown, the intraocular stent 100 may include additional openings, other than the end openings of the central lumen 106, for allowing fluid to pass therethrough. For example, a plurality of apertures 116 (which also may be referred to as "fenestrations") may be defined in the stent 100 and in fluid communication with the central lumen 106. As shown, the apertures 116 may be defined in the body 110 and extend from the circumferentially outer surface of the body 110 to the central lumen 106. In this manner, portions of fluid passing through the central lumen 106 may flow out of the stent 100 via the respective apertures 116. The apertures 116 collectively may define a fenestrated region 118 of the stent 100. In certain embodiments, upon implantation of the stent 100, the entirety, or at least a portion, of the fenestrated region 118 may reside within the suprachoroidal space, as shown in FIG. 1D. In this manner, aqueous humor flowing from the anterior chamber and through the stent 100 may exit the central lumen 106 via the apertures 116 or the distal end opening of the central lumen 106. In some embodiments, as shown, the apertures 116 may be arranged in one or more circumferential arrays extending along the entire circumference of the body 110. In other embodiments, only a partial circumferential array of the apertures 116 may be positioned along only a portion of the circumference of the body 110. In certain embodiments, as shown, the apertures 116 each may have a circular cross-sectional shape, taken in the direction perpendicular to the respective axes of the apertures 116, although other shapes of the apertures 116 may be used.

In certain embodiments, the intraocular stent 100 may be formed as a monolithic member. In other words, the body 110, the flange 112, and the retention rings 114 may be integrally formed with one another. In other embodiments, one or more portions of the stent 100 may be separately formed and attached to one or more remaining portions of the stent 100. The intraocular stent 100 may be formed of various materials. In certain embodiments, the stent 100 may be formed of polyimide, although other biocompatible materials suitable for implantation within the eye may be used. In certain embodiments, the stent may be formed of a semi-transparent material, although transparent or opaque materials may be used in other embodiments. In certain embodiments, the stent 100 may be sufficiently flexible enough to elastically bend in a direction transverse to the longitudinal axis $A_S$ yet sufficiently rigid to maintain patency of the central lumen 106 upon implantation (i.e., the stent 100 may resist forces exerted by surrounding tissue to maintain the central lumen 106 in an open state for fluid flow therethrough). It will be appreciated that the intraocular stent 100 may have various features, configurations, and/or properties in addition to, or instead of, those described above and illustrated in FIGS. 1A-1D.

Figures 2A, 2B:
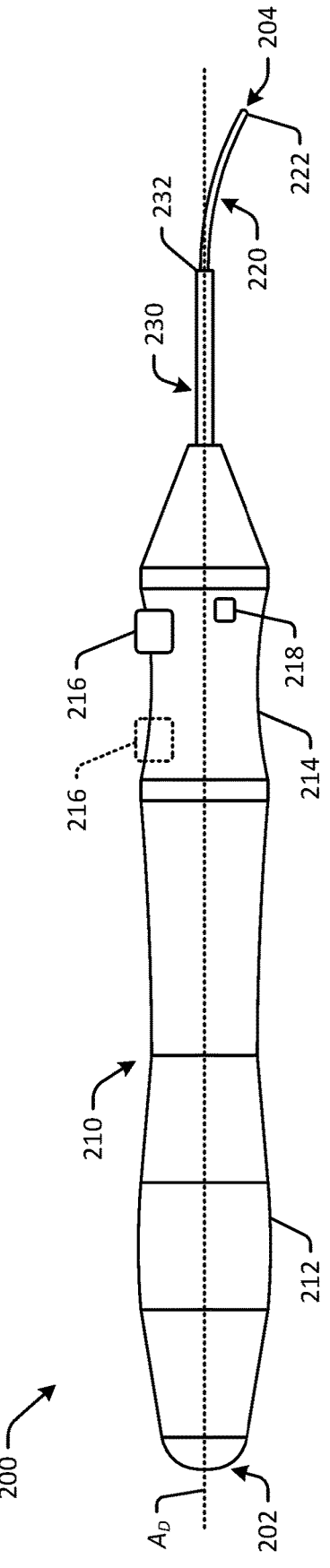
FIG. 2A is side view of a delivery device for implanting an intraocular stent in accordance with one or more embodiments of the disclosure.
FIG. 2B is a detailed perspective view of a distal portion of the delivery device of FIG. 2A, with the intraocular stent of FIG. 1A mounted thereto for implantation.

FIGS. 2A and 2B illustrate a delivery device 200 (which also may be referred to as a "delivery instrument," an "implantation device," or simply a "device") according to one or more embodiments of the disclosure. The delivery device 200 may be configured for implanting an intraocular stent, such as the intraocular stent 100 described above, within the eye of a patient for treatment of an eye disorder. Although use of the delivery device 200 is described specifically herein with respect to the intraocular stent 100, it will be appreciated that the delivery device 200 may be used in a similar manner for implanting various other types of stents or implantable devices.

The delivery device 200 may be formed as an elongated assembly having a longitudinal axis $A_D$ extending between a proximal end 202 (which also may be referred to as a "first end") and a distal end 204 (which also may be referred to as a "second end") of the device 200. As shown, the delivery device 200 may include a housing 210, a guide 220, and a tube 230 assembled to one another. The housing 210 may include a handle portion 212 extending distally from the proximal end 202 of the delivery device 200, and an actuating portion 214 disposed distally relative to the handle portion 212. The handle portion 212 may be configured to be grasped by the hand of a user (i.e., a surgeon) and manipulated during use of the delivery device 200 to guide a mounted intraocular implant to a desired implantation site. In some embodiments, the handle portion 212 may house additional internal components of the delivery device 200 therein. The actuating portion 214 may be configured to be manipulated by the user to control release of the intraocular stent from the delivery device 200. For example, a first actuator 216 may be movably disposed along the actuating portion 214 for controlling relative movement of the guide 220 and/or the tube 230 with respect to the housing 210. In certain embodiments, the first actuator 216 may be formed as a button configured to slidably translate relative to the housing 210, although other configurations may be used. For example, the first actuator 216 may be moved relative to the housing 210 from a first position, as shown in FIG. 2A, to a second position (shown via dashed lines) to move the guide 220 and/or the tube 230 relative to the housing 210 and release the mounted intraocular stent from the delivery device 200. A second actuator 218 also may be movably disposed along the actuating portion 214 for controlling components configured to illuminate the mounted intraocular stent, as described further below. In certain embodiments, the second actuator 218 may be formed as a button configured to be depressed relative to the housing 210, although other configurations may be used. For example, the second actuator 218 may be depressed relative to the housing 210 from a first position to a second position to cause additional components of the device 200 to illuminate the mounted intraocular stent. In this manner, the second actuator 218 may function as an ON-OFF button for controlling illumination of the stent mounted to the delivery device.

As shown, the guide 220 (which also may be referred to as a "guide member" or a "guide assembly") may have an elongated shape and may extend distally from the housing 210. The guide 220 may be configured to receive at least a portion of the mounted intraocular stent thereon. For example, at least a portion of the guide 220 may extend through the intraocular stent when the stent is mounted to the delivery device 200. The guide 200 also may be configured to penetrate ocular tissue to facilitate advancing the intraocular stent to a desired implantation site. In some embodiments, as shown, a distal end 222 of the guide 220 may be positioned outside of the housing 210, and a proximal end of the guide 220 may be positioned within the housing 210. In some embodiments, the distal end 222 may be tapered or sharpened to ease penetration of the guide 220 through ocular tissue. In other embodiments, the distal end 222 may be rounded to inhibit damage to ocular tissue as the guide 220 advances through the eye toward the implantation site. In certain embodiments, the guide 220 may be configured to move relative to the housing 210. For example, the guide 220 may be translatably attached to the housing 210 and configured to translate between an extended position, as shown in FIG. 2A, and a retracted position in which at least a portion of the guide 220 moves from outside of the housing 210 to within the housing 210. In certain embodiments, at least a portion of the guide 220 may be flexible to facilitate advancement of the guide 220 and the intraocular stent to the desired implantation site. In other embodiments, the entire guide 220 may be rigid. In certain embodiments, as shown, at least a portion of the guide 220, such as a distal portion thereof, may have a predefined curved shape to facilitate navigating through ocular tissue to the implantation site. In other embodiments, the entire guide 220 may have a straight, linear shape.

As shown, the tube 230 (which also may be referred to as an "outer tube," a "drive tube," or a "sheath") may have an elongated shape and may extend distally from the housing 210. In some embodiments, as shown, a distal end 232 of the tube 230 may be positioned outside of the housing 210, and a proximal end of the tube 230 may be positioned within the housing 210. The tube 230 may be configured to engage a portion of an intraocular stent mounted to the delivery device 200. For example, the distal end 232 of the tube 230 may be configured to abut a mating end of the mounted intraocular stent to facilitate driving the stent through ocular tissue to a desired implantation site. In certain embodiments, the tube 230 may be fixed relative to the housing 210. In other words, the tube 230 may be fixedly attached to the housing 210 such that the tube 230 does not move relative to the housing 210. In this manner, when the guide 220 is moved from the extended position to the retracted position, as described above, the tube 230 may prevent the intraocular stent from moving along with the guide 220, thereby facilitating release of the stent from the delivery device 200.

The intraocular stent 100 may be mounted to the distal portion of the delivery device 200 as shown in FIG. 2B. In certain embodiments, the stent 100 may be positioned over a portion of the guide 220, such that the guide 220 extends through the central lumen 106 of the stent 100 and the distal end 222 of the guide 220 is exposed beyond the distal end 104 of the stent 100. In this manner, the guide 220 may be inserted into a patient's eye and guide advancement of the stent 100 through the ocular tissue. In certain embodiments, a friction fit may be formed between the circumferentially outer surface of the guide 220 and the circumferentially inner surface of the central lumen 106 to facilitate retention of the stent 100 on the guide 220. Further, the stent 100 may engage the tube 230 when mounted to the delivery device 200 for implantation. In certain embodiments, as shown, the distal end 232 of the tube 230 may abut the proximal end 102 of the stent 100, such that the stent 100 is prevented from moving proximally toward the housing 210 of the device 200. In this manner, the engagement between the tube 230 and the stent 100 may facilitate driving the stent 100 through the ocular tissue to the desired implantation site. As described above, once the stent 100 is advanced to the implantation site, such as with the stent 100 positioned between the anterior chamber and the suprachoroidal space, as shown in FIG. 1D, the stent 100 may be released from the delivery device 200. For example, the first actuator 216 may be moved from the first position to the second position, thereby moving the guide 220 from the extended position to the retracted position. Such movement of the guide 220 may remove the guide 220 from the central lumen 106 of the stent 100, while the tube 230 prevents movement of the stent 100 relative to the tube 230 and the housing 210. The stent 100 thus may become disengaged from the delivery device 200, and the device 200 may be removed from the patient.

FIGS. 3A-3C illustrate a delivery device assembly 300 (which also may be referred to as a "delivery device" or simply as an "assembly") according to one or more embodiments of the disclosure. The delivery device assembly 300 may be used with the delivery device 200 described above. In other words, the assembly 300 may form a portion of the delivery device 200. As shown, the assembly 300 may include a guide 320 (which also may be referred to as a "guide member"), a tube 330 (which also may be referred to as an "outer tube," a "drive tube," or a "sheath"), a fiber optic cable 340, and a light source 350. The guide 320 and the tube 330 generally may be configured to function in a manner similar to the guide 220 and the tube 230 of the delivery device 200 described above, although certain differences are described herein.

The guide 320 may be formed as an elongated member having a distal end 322 and a proximal end 324 positioned opposite one another in a direction of the longitudinal axis thereof. In some embodiments, the guide 320 may have a solid, cylindrical shape, as shown. In other embodiments, the guide 320 may have a tubular, cylindrical shape. In some embodiments, the guide 320 may be formed of a rigid or substantially rigid material, such as a metal or a polymer. In some embodiments, the guide 320 may have a straight, linear shape. In other embodiments, at least a portion of the guide 320, such as a distal portion thereof, may have a predefined curved shape. The guide 320 may be configured for guiding an intraocular stent, such as the stent 100, through ocular tissue during an implantation procedure.

The tube 330 may be formed as an elongated tubular member having a distal end 332 and a proximal end 334 positioned opposite one another in a direction of the longitudinal axis thereof. The tube 330 generally may be configured in the same manner as the tube 230 described above.

The fiber optic cable 340 may be formed as an elongated member having a distal end 342 and a proximal end 344 positioned opposite one another in a direction of the longitudinal axis thereof. In some embodiments, as shown, the fiber optic cable 340 may have a cylindrical shape, although other shapes may be used. The fiber optic cable 340 may include one or more optical fibers configured to carry light. As shown, the proximal end 344 of the fiber optic cable 340 may be in communication with the light source 350 for receiving light therefrom. The distal end 342 of the fiber optic cable 340 may engage the proximal end 324 of the guide 320, as shown. In some embodiments, the fiber optic cable 340 and the guide 320 may be attached, either fixedly or releasably, to one another by one or more attachment mechanism. As shown, the fiber optic cable 340 may extend through the tube 330. In certain embodiments, the fiber optic cable 340 may include a textured region 346 (shown via cross-hatching in FIGS. 3A and 3C). The textured region 346 may be a rough surface formed along the fiber optic cable 340 and configured to diffuse light transmitted by the fiber optic cable 340. Various techniques for forming the textured surface 346 may be used, such as rubbing the fiber optic cable 340 with an abrasive material. In certain embodiments, as shown, the textured region 346 may be formed along the outer circumferential surface of the fiber optic cable 340. In some embodiments, the textured region 346 may extend from the distal end 342 of the fiber optic cable 340 toward the proximal end 344 thereof. In other embodiments, the textured region 346 may be spaced apart from the distal end 342. In some embodiments, the textured region 346 may extend along the entire circumference of the fiber optic cable 340. In other embodiments, the textured region 346 may extend along only a portion of the circumference of the fiber optic cable 340. In certain embodiments, as shown, the respective longitudinal axes of the guide 320, the tube 330, and the fiber optic cable 340 may be coaxial with one another.

The light source 350 may be any type of light source configured to produce light and transmit the light to the fiber optic cable 340. In some embodiments, the light source 350 may be a laser light source, although other types of devices for producing light may be used.

In certain embodiments, the assembly 300 may be used as a part of the delivery device 200 described above. In such embodiments, the light source 350 may be positioned within the housing 210 and in communication with the second actuator 218 for activating and deactivating the light source 350. The proximal end 344 of the fiber optic cable 340 may be positioned within the housing 210, while the distal end 342 thereof may be positioned outside of the housing 210. Further, a portion of the fiber optic cable 340 may be attached to, either directly or indirectly, or otherwise in mechanical communication with the first actuator 216 for translating the fiber optic cable 340 and the guide 320 between an extended position and a retracted position for controlling release of an intraocular stent from the delivery device 200. The tube 330 may be fixed to the housing 210, with the proximal end 334 of the tube 330 positioned within the housing 210 and the distal end 332 thereof positioned outside of the housing 210. The tube 330 may be configured for driving the intraocular stent through ocular tissue during use of the delivery device 200, as described above.

FIGS. 3B and 3C illustrate the assembly 300 with the intraocular stent 100 mounted thereto. As shown, the stent 100 may be positioned over a portion of the guide 320 and over a portion of the fiber optic cable 340, such that the subassembly of the guide 320 and the fiber optic cable 340 extends through the central lumen 106 of the stent 100 and the distal end 322 of the guide 220 is exposed beyond the distal end 104 of the stent 100. In this manner, the guide 320 may be inserted into a patient's eye and guide advancement of the stent 100 through the ocular tissue. In certain embodiments, a friction fit may be formed between the circumferentially outer surface of the guide 320 and the circumferentially inner surface of the central lumen 106 and/or between the circumferentially outer surface of the fiber optic cable 340 and the circumferentially inner surface of the central lumen 106 to facilitate retention of the stent 100 on the delivery device 200. Further, the stent 100 may engage the tube 330 when mounted to the delivery device 200 for implantation. In certain embodiments, as shown, the distal end 332 of the tube 230 may abut the proximal end 102 of the stent 100, such that the stent 100 is prevented from moving proximally toward the housing 210 of the device 200. In this manner, the engagement between the tube 330 and the stent 100 may facilitate driving the stent 100 through the ocular tissue to the desired implantation site. In certain embodiments, as shown, the respective longitudinal axes of the guide 320, the tube 330, and the fiber optic cable 340 may be coaxial with one another and coaxial with the longitudinal axis of the stent 100 mounted to the delivery device 200. As described above, once the stent 100 is advanced to the implantation site, such as with the stent 100 positioned between the anterior chamber and the suprachoroidal space, as shown in FIG. 1D, the stent 100 may be released from the delivery device 200. For example, the first actuator 216 may be moved from the first position to the second position, thereby moving the guide 320 and the fiber optic cable 340 from the extended position to the retracted position. Such movement of the guide 320 and the fiber optic cable 340 may remove the guide 320 and the fiber optic cable 340 from the central lumen 106 of the stent 100, while the tube 330 prevents movement of the stent 100 relative to the tube 330 and the housing 210. The stent 100 thus may become disengaged from the delivery device 200, and the device 200 may be removed from the patient.

During the implantation procedure, such as during insertion of the intraocular stent 100 into the patient's eye and movement of the stent 100 toward the desired implantation site, the assembly 300 may be used to illuminate the stent 100. For example, the second actuator 218 may be moved to the on position to activate the light source 350. The light generated by the light source 350 may be delivered to and transmitted by the fiber optic cable 340. The received light may be diffused by the fiber optic cable 340, particularly the textured region 346 thereof. In this manner, the light carried by the fiber optic cable 340 may illuminate the stent 100. In certain embodiments, as shown, the textured region 346 may be positioned entirely within the central lumen 106 of the stent 100 when the stent 100 is mounted to the delivery device 200 and the subassembly of the guide 320 and the fiber optic cable 340 is in the extended position. In some embodiments, the axial length of the textured region 346 may be less than the axial length of the stent 100. In other embodiments, the axial length of the textured region 346 may be equal to the axial length of the stent 100. Ultimately, the illumination of the stent 100 achieved by the assembly 300 may allow the surgeon to easily visualize the stent 100 during the implantation procedure and confidently direct the stent 100 to the desired implantation site.

Figures 4A, 4B, 4C:
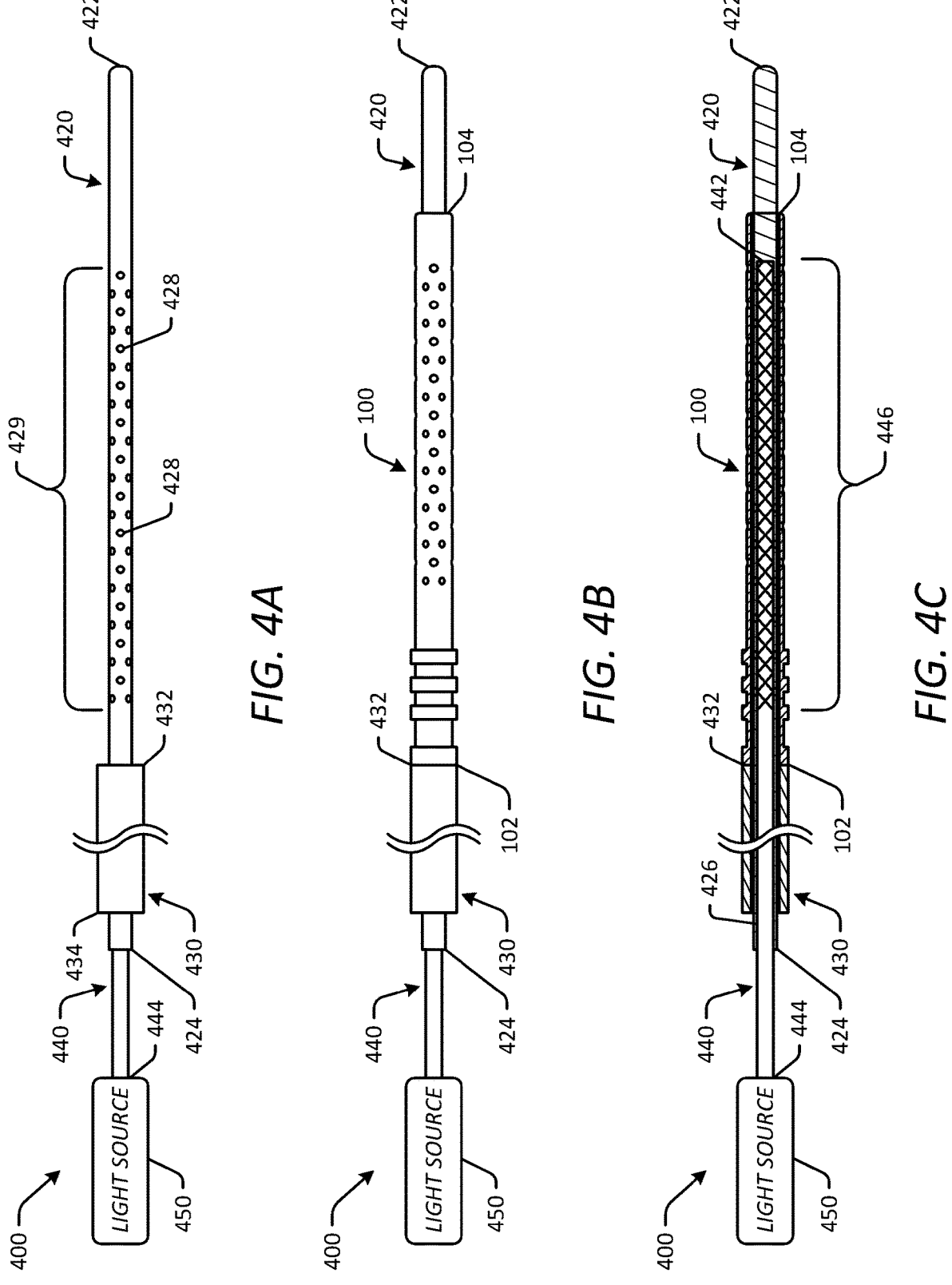
FIG. 4A is a side view of a portion of a delivery device for implanting an intraocular stent in accordance with one or more embodiments of the disclosure, as may be used with the delivery device of FIG. 2A.
FIG. 4B is a side view of the portion of the delivery device of FIG. 4A, with the intraocular stent of FIG. 1A mounted thereto for implantation.
FIG. 4C is a partial cross-sectional side view of the portion of the delivery device of FIG. 4A and the intraocular stent of FIG. 1A.

FIGS. 4A-4C illustrate a delivery device assembly 400 (which also may be referred to as a "delivery device" or simply as an "assembly") according to one or more embodiments of the disclosure. The delivery device assembly 400 may be used with the delivery device 200 described above. In other words, the assembly 400 may form a portion of the delivery device 200. As shown, the assembly 400 may include a guide 420 (which also may be referred to as a "guide member"), a tube 430 (which also may be referred to as an "outer tube," a "drive tube," or a "sheath"), a fiber optic cable 440, and a light source 450. The guide 420 and the tube 430 generally may be configured to function in a manner similar to the guide 220 and the tube 230 of the delivery device 200 described above, although certain differences are described herein.

The guide 420 may be formed as an elongated member having a distal end 422 and a proximal end 424 positioned opposite one another in a direction of the longitudinal axis thereof. In some embodiments, as shown, a distal portion of the guide 420 may have a solid, cylindrical shape, and a proximal portion of the guide 420 may have a tubular, cylindrical shape defining a central bore 426 therein. In other words, the central bore 426 may be formed as a blind hole extending along the longitudinal axis of the guide 420. In other embodiments, the guide 420 may have a tubular, cylindrical shape defining the central bore 426 therein. In other words, the central bore 426 may be formed as a through hole extending along the longitudinal axis of the guide 420. In some embodiments, as shown, the guide 420 also may include a plurality of apertures 428 defined therein, with each aperture 428 extending transverse to the longitudinal axis of the guide 420. For example, each aperture 428 may extend perpendicular to the longitudinal axis of the guide 420. The apertures 428 collectively may define an apertured region 429 of the guide 420. In some embodiments, as shown, the apertures 428 may be arranged in one or more circumferential arrays extending along the entire circumference of the guide 420. In other embodiments, only a partial circumferential array of the apertures 428 may be positioned along only a portion of the circumference of the guide 420. In certain embodiments, as shown, the apertures 428 each may have a circular cross-sectional shape, taken in the direction perpendicular to the respective axes of the apertures 428, although other shapes of the apertures 428 may be used. In some embodiments, as shown, the apertures 428 may be formed as through holes extending from the outer circumferential surface of the guide 420 to the central bore 426. In other embodiments, the apertures 428 may be formed as blind holes extending from the outer circumferential surface of the guide 420 toward, but not to, the central bore 426 or extending from the central bore 426 toward, but not to, the outer circumferential surface of the guide 420. In some embodiments, the guide 420 may be formed of a rigid or substantially rigid material, such as a metal or a polymer. In some embodiments, the guide 420 may have a straight, linear shape. In other embodiments, at least a portion of the guide 420, such as a distal portion thereof, may have a predefined curved shape. The guide 420 may be configured for guiding an intraocular stent, such as the stent 100, through ocular tissue during an implantation procedure.

The tube 430 may be formed as an elongated tubular member having a distal end 432 and a proximal end 434 positioned opposite one another in a direction of the longitudinal axis thereof. The tube 430 generally may be configured in the same manner as the tube 230 described above.

The fiber optic cable 440 may be formed as an elongated member having a distal end 442 and a proximal end 444 positioned opposite one another in a direction of the longitudinal axis thereof. In some embodiments, as shown, the fiber optic cable 440 may have a cylindrical shape, although other shapes may be used. The fiber optic cable 440 may include one or more optical fibers configured to carry light. As shown, the proximal end 444 of the fiber optic cable 440 may be in communication with the light source 450 for receiving light therefrom. As shown, a portion of the fiber optic cable 440 may be positioned within the central bore 426 of the guide 420, and the distal end 442 of the fiber optic cable 440 may engage the end of the central bore 426 in embodiments in which the central bore 426 is formed as a blind hole. In some embodiments, the fiber optic cable 440 and the guide 420 may be attached, either fixedly or releasably, to one another by one or more attachment mechanism. For example, the fiber optic cable 440 may be attached to the guide 420 by a friction fiction connection within the central bore 426, although additional or alternative attachment mechanisms may be used. As shown, the fiber optic cable 440 may extend through the tube 430. In certain embodiments, the fiber optic cable 440 may include a textured region 446 (shown via cross-hatching in FIG. 4C). The textured region 446 may be a rough surface formed along the fiber optic cable 440 and configured to diffuse light transmitted by the fiber optic cable 440. Various techniques for forming the textured surface 446 may be used, such as rubbing the fiber optic cable 440 with an abrasive material. In certain embodiments, as shown, the textured region 446 may be formed along the outer circumferential surface of the fiber optic cable 440. In some embodiments, the textured region 446 may extend from the distal end 442 of the fiber optic cable 440 toward the proximal end 444 thereof. In other embodiments, the textured region 446 may be spaced apart from the distal end 442. In some embodiments, the textured region 446 may extend along the entire circumference of the fiber optic cable 440. In other embodiments, the textured region 446 may extend along only a portion of the circumference of the fiber optic cable 440. In certain embodiments, as shown, the respective longitudinal axes of the guide 420, the tube 430, and the fiber optic cable 440 may be coaxial with one another.

The light source 450 may be any type of light source configured to produce light and transmit the light to the fiber optic cable 440. In some embodiments, the light source 450 may be a laser light source, although other types of devices for producing light may be used.

In certain embodiments, the assembly 400 may be used as a part of the delivery device 200 described above. In such embodiments, the light source 450 may be positioned within the housing 210 and in communication with the second actuator 218 for activating and deactivating the light source 450. The proximal end 444 of the fiber optic cable 440 may be positioned within the housing 210, while the distal end 442 thereof may be positioned outside of the housing 210. The tube 430 may be fixed to the housing 210, with the proximal end 434 of the tube 430 positioned within the housing 210 and the distal end 432 thereof positioned outside of the housing 210. The tube 430 may be configured for driving the intraocular stent through ocular tissue during use of the delivery device 200, as described above. The guide 420 may be movably attached to the housing 210 and configured to translate relative to the housing 210 between an extended position and a retracted position, similar to the guide 220 described above. Further, a portion of the guide 420 may be attached to, either directly or indirectly, or otherwise in mechanical communication with the first actuator 216 for translating the guide 420 between the extended position and the retracted position for controlling release of an intraocular stent from the delivery device 200.

FIGS. 4B and 4C illustrate the assembly 400 with the intraocular stent 100 mounted thereto. As shown, the stent 100 may be positioned over a portion of the guide 420 and over a portion of the fiber optic cable 440, such that the subassembly of the guide 420 and the fiber optic cable 440 extends through the central lumen 106 of the stent 100 and the distal end 422 of the guide 420 is exposed beyond the distal end 104 of the stent 100. In this manner, the guide 420 may be inserted into a patient's eye and guide advancement of the stent 100 through the ocular tissue. In certain embodiments, a friction fit may be formed between the circumferentially outer surface of the guide 420 and the circumferentially inner surface of the central lumen 106 to facilitate retention of the stent 100 on the delivery device 200. Further, the stent 100 may engage the tube 430 when mounted to the delivery device 200 for implantation. In certain embodiments, as shown, the distal end 432 of the tube 430 may abut the proximal end 102 of the stent 100, such that the stent 100 is prevented from moving proximally toward the housing 210 of the device 200. In this manner, the engagement between the tube 430 and the stent 100 may facilitate driving the stent 100 through the ocular tissue to the desired implantation site. In certain embodiments, as shown, the respective longitudinal axes of the guide 420, the tube 430, and the fiber optic cable 440 may be coaxial with one another and coaxial with the longitudinal axis of the stent 100 mounted to the delivery device 200. As described above, once the stent 100 is advanced to the implantation site, such as with the stent 100 positioned between anterior chamber and the suprachoroidal space, as shown in FIG. 1D, the stent 100 may be released from the delivery device 200. For example, the first actuator 216 may be moved from the first position to the second position, thereby moving the guide 420 and the fiber optic cable 440 from the extended position to the retracted position. Such movement of the guide 420 and the fiber optic cable 440 may remove the guide 420 and the fiber optic cable 440 from the central lumen 106 of the stent 100, while the tube 430 prevents movement of the stent 100 relative to the tube 430 and the housing 210. The stent 100 thus may become disengaged from the delivery device 200, and the device 200 may be removed from the patient.

During the implantation procedure, such as during insertion of the intraocular stent 100 into the patient's eye and movement of the stent 100 toward the desired implantation site, the assembly 400 may be used to illuminate the stent 100. For example, the second actuator 218 may be moved to the on position to activate the light source 450. The light generated by the light source 450 may be delivered to and transmitted by the fiber optic cable 440. The received light may be diffused by the fiber optic cable 440, particularly the textured region 446 thereof. In this manner, the light carried by the fiber optic cable 440 may pass through the apertures 428 of the guide 420 and illuminate the stent 100. In certain embodiments, as shown, the textured region 446 may be positioned entirely within the central lumen 106 of the stent 100 when the stent 100 is mounted to the delivery device 200 and the subassembly of the guide 420 and the fiber optic cable 440 is in the extended position. In some embodiments, the axial length of the textured region 446 may be less than the axial length of the stent 100. In other embodiments, the axial length of the textured region 446 may be equal to the axial length of the stent 100. In certain embodiments, as shown, the apertured region 429 may be positioned entirely within the central lumen 106 of the stent 100 when the stent 100 is mounted to the delivery device 200 and the subassembly of the guide 420 and the fiber optic cable 440 is in the extended position. In some embodiments, the axial length of the apertured region 429 may be less than the axial length of the stent 100. In other embodiments, the axial length of the apertured region 429 may be equal to the axial length of the stent 100. Ultimately, the illumination of the stent 100 achieved by the assembly 400 may allow the surgeon to easily visualize the stent 100 during the implantation procedure and confidently direct the stent 100 to the desired implantation site.

FIGS. 5A-5E illustrate a delivery device assembly 500 (which also may be referred to as a "delivery device" or simply as an "assembly") according to one or more embodiments of the disclosure. The delivery device assembly 500 may be used with the delivery device 200 described above. In other words, the assembly 500 may form a portion of the delivery device 200. As shown, the assembly 500 may include a guide 520 (which also may be referred to as a "guide member"), a tube 530 (which also may be referred to as an "outer tube," a "drive tube," or a "sheath"), a fiber optic cable 540, and a light source 550. The guide 520 and the tube 530 generally may be configured to function in a manner similar to the guide 220 and the tube 230 of the delivery device 200 described above, although certain differences are described herein.

The guide 520 may be formed as an elongated member having a distal end 522 and a proximal end 524 positioned opposite one another in a direction of the longitudinal axis thereof. In some embodiments, as shown, a distal portion of the guide 520 may have a solid, cylindrical shape, and a proximal portion of the guide 520 may have a partially tubular, cylindrical shape defining a central passage 526 therein. As shown, the central passage 526 may be formed as an open channel extending along the longitudinal axis of the guide 520 and open along at least a portion of the outer circumferential surface of the guide 520. In some embodiments, as shown, the guide 520 also may include a plurality of apertures 528 defined therein, with each aperture 528 extending transverse to the longitudinal axis of the guide 520. For example, each aperture 528 may extend perpendicular to the longitudinal axis of the guide 520. The apertures 528 collectively may define an apertured region 529 of the guide 520. In some embodiments, as shown, only a partial circumferential array of the apertures 528 may be positioned along only a portion of the circumference of the guide 520 (i.e., the portion of the circumference not exposed by the central passage 526). In certain embodiments, as shown, the apertures 528 each may have a circular cross-sectional shape, taken in the direction perpendicular to the respective axes of the apertures 528, although other shapes of the apertures 528 may be used. In some embodiments, as shown, the apertures 528 may be formed as through holes extending from the outer circumferential surface of the guide 520 to the central passage 526. In other embodiments, the apertures 528 may be formed as blind holes extending from the outer circumferential surface of the guide 520 toward, but not to, the central passage 526 or extending from the central passage 526 toward, but not to, the outer circumferential surface of the guide 520. In some embodiments, the guide 520 may be formed of a rigid or substantially rigid material, such as a metal or a polymer. In some embodiments, the guide 520 may have a straight, linear shape. In other embodiments, at least a portion of the guide 520, such as a distal portion thereof, may have a predefined curved shape. The guide 520 may be configured for guiding an intraocular stent, such as the stent 100, through ocular tissue during an implantation procedure.

The tube 530 may be formed as an elongated tubular member having a distal end 532 and a proximal end 534 positioned opposite one another in a direction of the longitudinal axis thereof. The tube 530 generally may be configured in the same manner as the tube 230 described above.

The fiber optic cable 540 may be formed as an elongated member having a distal end 542 and a proximal end 544 positioned opposite one another in a direction of the longitudinal axis thereof. In some embodiments, as shown, the fiber optic cable 540 may have a cylindrical shape, although other shapes may be used. The fiber optic cable 540 may include one or more optical fibers configured to carry light.

As shown, the proximal end 544 of the fiber optic cable 540 may be in communication with the light source 550 for receiving light therefrom. As shown, a portion of the fiber optic cable 540 may be positioned within the central passage 526 of the guide 520, and the distal end 542 of the fiber optic cable 540 may engage the end of the central passage 526 in embodiments in which the central passage 526 does not extend to the distal end 522 of the guide 520. In some embodiments, the fiber optic cable 540 and the guide 520 may be attached, either fixedly or releasably, to one another by one or more attachment mechanism. For example, the fiber optic cable 540 may be attached to the guide 520 by a friction fiction connection within the central passage 526, although additional or alternative attachment mechanisms may be used. As shown, the fiber optic cable 540 may extend through the tube 530. In certain embodiments, the fiber optic cable 540 may include a textured region 546 (shown via cross-hatching in FIG. 4C). The textured region 546 may be a rough surface formed along the fiber optic cable 540 and configured to diffuse light transmitted by the fiber optic cable 540. Various techniques for forming the textured surface 546 may be used, such as rubbing the fiber optic cable 540 with an abrasive material. In certain embodiments, as shown, the textured region 546 may be formed along the outer circumferential surface of the fiber optic cable 540. In some embodiments, the textured region 546 may extend from the distal end 542 of the fiber optic cable 540 toward the proximal end 544 thereof. In other embodiments, the textured region 546 may be spaced apart from the distal end 542. In some embodiments, the textured region 546 may extend along the entire circumference of the fiber optic cable 540. In other embodiments, the textured region 546 may extend along only a portion of the circumference of the fiber optic cable 540. In certain embodiments, as shown, the respective longitudinal axes of the guide 520 and the tube 530 may be coaxial with one another, and the longitudinal axis of the fiber optic cable 540 may be offset from the longitudinal axes of the guide 520 and the tube 530. In other embodiments, the respective longitudinal axes of the guide 520, the tube 530, and the fiber optic cable 540 may be coaxial with one another.

The light source 550 may be any type of light source configured to produce light and transmit the light to the fiber optic cable 540. In some embodiments, the light source 550 may be a laser light source, although other types of devices for producing light may be used.

In certain embodiments, the assembly 500 may be used as a part of the delivery device 200 described above. In such embodiments, the light source 550 may be positioned within the housing 210 and in communication with the second actuator 218 for activating and deactivating the light source 550. The proximal end 544 of the fiber optic cable 540 may be positioned within the housing 210, while the distal end 542 thereof may be positioned outside of the housing 210. The tube 530 may be fixed to the housing 210, with the proximal end 534 of the tube 530 positioned within the housing 210 and the distal end 532 thereof positioned outside of the housing 210. The tube 530 may be configured for driving the intraocular stent through ocular tissue during use of the delivery device 200, as described above. The guide 520 may be movably attached to the housing 210 and configured to translate relative to the housing 210 between an extended position and a retracted position, similar to the guide 220 described above. Further, a portion of the guide 520 may be attached to, either directly or indirectly, or otherwise in mechanical communication with the first actuator 216 for translating the guide 520 between the extended position and the retracted position for controlling release of an intraocular stent from the delivery device 200.

Figures 5A, 5B, 5C:
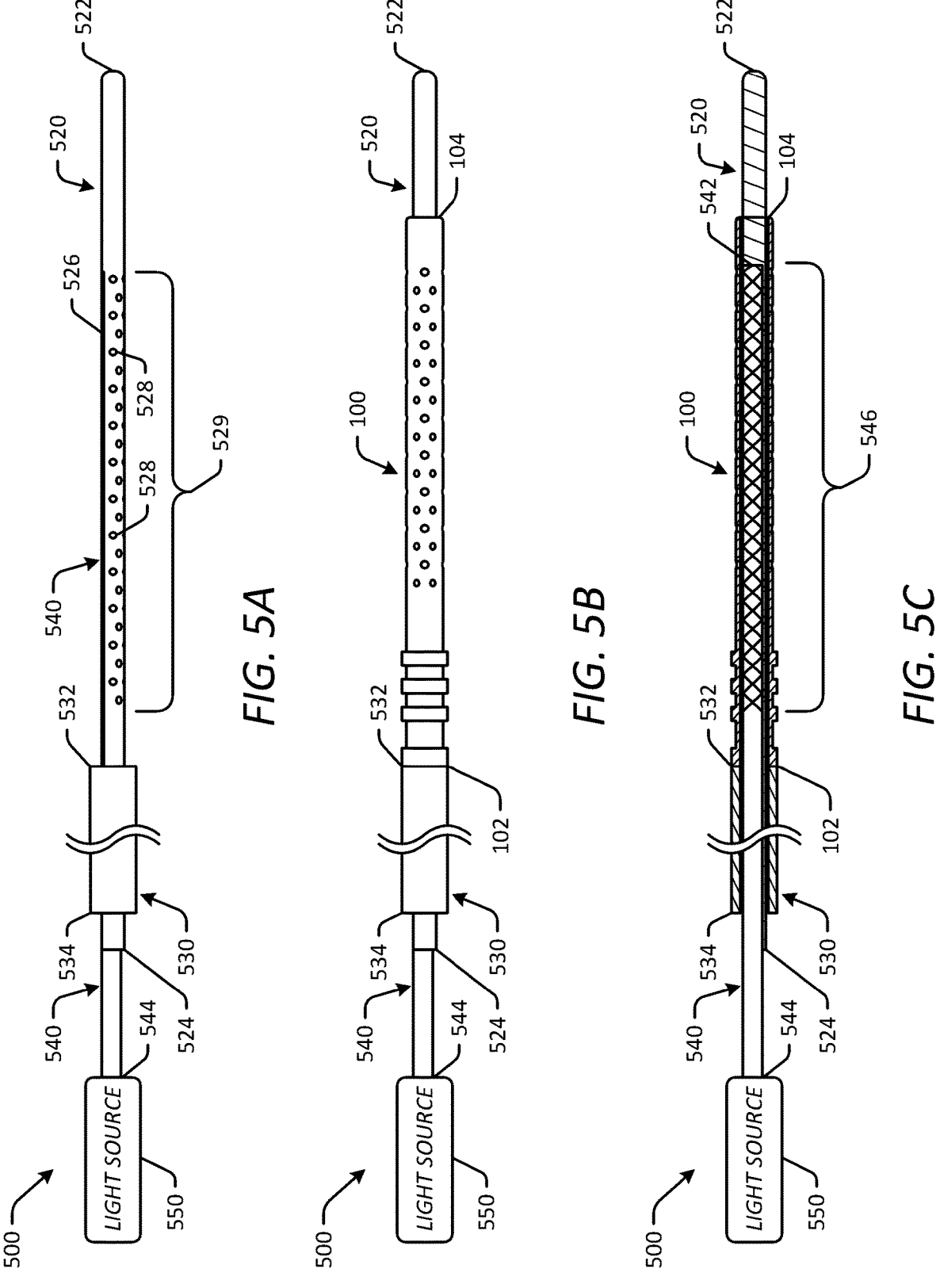
FIG. 5A is a side view of a portion of a delivery device for implanting an intraocular stent in accordance with one or more embodiments of the disclosure, as may be used with the delivery device of FIG. 2A.
FIG. 5B is a side view of the portion of the delivery device of FIG. 5A, with the intraocular stent of FIG. 1A mounted thereto for implantation.
FIG. 5C is a partial cross-sectional side view of the portion of the delivery device of FIG. 5A and the intraocular stent of FIG. 1A.
Figures 5D, 5E:
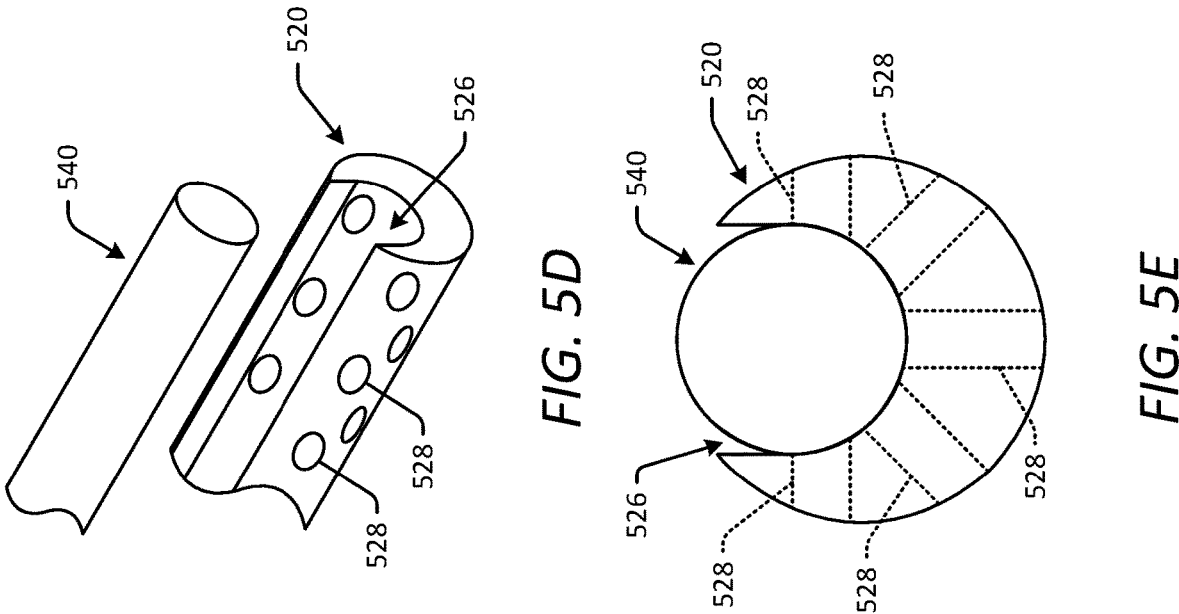
FIG. 5D is a detailed exploded perspective view of respective portions of a fiber optic cable and a guide member of the portion of the delivery device of FIG. 5A.
FIG. 5E is a detailed end view of the respective portions of the fiber optic cable and the guide member of the portion of the delivery device of FIG. 5A.

FIGS. 5B and 5C illustrate the assembly 500 with the intraocular stent 100 mounted thereto. As shown, the stent 100 may be positioned over a portion of the guide 520 and over a portion of the fiber optic cable 540, such that the subassembly of the guide 520 and the fiber optic cable 540 extends through the central lumen 106 of the stent 100 and the distal end 522 of the guide 520 is exposed beyond the distal end 104 of the stent 100. In this manner, the guide 520 may be inserted into a patient's eye and guide advancement of the stent 100 through the ocular tissue. In certain embodiments, a friction fit may be formed between the circumferentially outer surface of the guide 520 and the circumferentially inner surface of the central lumen 106 to facilitate retention of the stent 100 on the delivery device 200. Further, the stent 100 may engage the tube 530 when mounted to the delivery device 200 for implantation. In certain embodiments, as shown, the distal end 532 of the tube 430 may abut the proximal end 102 of the stent 100, such that the stent 100 is prevented from moving proximally toward the housing 210 of the device 200. In this manner, the engagement between the tube 530 and the stent 100 may facilitate driving the stent 100 through the ocular tissue to the desired implantation site. In certain embodiments, as shown, the respective longitudinal axes of the guide 520 and the tube 530 may be coaxial with one another and coaxial with the longitudinal axis of the stent 100 mounted to the delivery device 200, and the longitudinal axis of the fiber optic cable 540 may be offset from the longitudinal axis of the stent 100. In other embodiments, the respective longitudinal axes of the guide 520, the tube 530, and the fiber optic cable 540 may be coaxial with one another and coaxial with the longitudinal axis of the stent 100 mounted to the delivery device 200. As described above, once the stent 100 is advanced to the implantation site, such as with the stent 100 positioned between the anterior chamber and the suprachoroidal space, as shown in FIG. 1D, the stent 100 may be released from the delivery device 200. For example, the first actuator 216 may be moved from the first position to the second position, thereby moving the guide 520 and the fiber optic cable 540 from the extended position to the retracted position. Such movement of the guide 520 and the fiber optic cable 540 may remove the guide 520 and the fiber optic cable 540 from the central lumen 106 of the stent 100, while the tube 530 prevents movement of the stent 100 relative to the tube 530 and the housing 210. The stent 100 thus may become disengaged from the delivery device 200, and the device 200 may be removed from the patient.

During the implantation procedure, such as during insertion of the intraocular stent 100 into the patient's eye and movement of the stent 100 toward the desired implantation site, the assembly 500 may be used to illuminate the stent 100. For example, the second actuator 218 may be moved to the on position to activate the light source 550. The light generated by the light source 550 may be delivered to and transmitted by the fiber optic cable 540. The received light may be diffused by the fiber optic cable 540, particularly the textured region 546 thereof. In this manner, the light carried by the fiber optic cable 540 may pass through the apertures 528 and the open side of the central passage 526 of the guide 520 and illuminate the stent 100. In certain embodiments, as shown, the textured region 546 may be positioned entirely within the central lumen 106 of the stent 100 when the stent 100 is mounted to the delivery device 200 and the subassembly of the guide 520 and the fiber optic cable 540 is in the extended position. In some embodiments, the axial length of the textured region 546 may be less than the axial length of the stent 100. In other embodiments, the axial length of the textured region 546 may be equal to the axial length of the stent 100. In certain embodiments, as shown, the apertured region 529 may be positioned entirely within the central lumen 106 of the stent 100 when the stent 100 is mounted to the delivery device 200 and the subassembly of the guide 520 and the fiber optic cable 540 is in the extended position. In some embodiments, the axial length of the apertured region 529 may be less than the axial length of the stent 100. In other embodiments, the axial length of the apertured region 529 may be equal to the axial length of the stent 100. Ultimately, the illumination of the stent 100 achieved by the assembly 500 may allow the surgeon to easily visualize the stent 100 during the implantation procedure and confidently direct the stent 100 to the desired implantation site.

FIGS. 6A-6E illustrate a delivery device assembly 600 (which also may be referred to as a "delivery device" or simply as an "assembly") according to one or more embodiments of the disclosure. The delivery device assembly 600 may be used with the delivery device 200 described above. In other words, the assembly 600 may form a portion of the delivery device 200. As shown, the assembly 600 may include a guide 620 (which also may be referred to as a "guide member"), a tube 630 (which also may be referred to as an "outer tube," a "drive tube," or a "sheath"), a fiber optic tube 640, and a light source 650. The guide 620 and the tube 630 generally may be configured to function in a manner similar to the guide 220 and the tube 230 of the delivery device 200 described above, although certain differences are described herein.

The guide 620 may be formed as an elongated member having a distal end 622 and a proximal end 624 positioned opposite one another in a direction of the longitudinal axis thereof. In some embodiments, as shown, the guide 620 may have a solid, cylindrical shape. In other embodiments, the guide 620 may have a tubular, cylindrical shape defining a central bore therein. In some embodiments, the guide 620 may be formed of a rigid or substantially rigid material, such as a metal or a polymer. In some embodiments, the guide 620 may have a straight, linear shape. In other embodiments, at least a portion of the guide 620, such as a distal portion thereof, may have a predefined curved shape. The guide 620 may be configured for guiding an intraocular stent, such as the stent 100, through ocular tissue during an implantation procedure.

The tube 630 may be formed as an elongated tubular member having a distal end 632 and a proximal end 634 positioned opposite one another in a direction of the longitudinal axis thereof. The tube 630 generally may be configured in the same manner as the tube 230 described above.

The fiber optic tube 640 may be formed as an elongated assembly having a distal end 642 and a proximal end 644 positioned opposite one another in a direction of the longitudinal axis thereof. In some embodiments, as shown, the fiber optic tube 640 may have a tubular cylindrical shape, although other shapes may be used. The fiber optic tube 640 may include a tubular casing 646 and one or more fiber optic cables 648 positioned within a wall thickness of the tubular casing 646. In other words, each fiber optic cable 648 may be positioned within the wall of the tubular casing 646, between the outer circumferential surface and the inner circumferential surface thereof, as shown in FIGS. 6D and 6E. In certain embodiments, as shown, the fiber optic cables 648 may be positioned in a circumferential array about the longitudinal axis of the fiber optic tube 640. Each fiber optic cable 648 may extend from the proximal end 644 to the distal end 642 of the fiber optic tube 640 and may include one or more optical fibers configured to carry light. As shown, the proximal end 644 of the fiber optic tube 640, and the proximal ends of the fiber optic cables 648 thereof, may be in communication with the light source 650 for receiving light therefrom. As shown, a portion of the fiber optic tube 640 may be positioned within the central lumen of the tube 630. In certain embodiments, as shown, the distal end 642 of the fiber optic tube 640, and the distal ends of the fiber optic cables 648, may be flush with the distal end 632 of the tube 630. In certain embodiments, as shown, the respective longitudinal axes of the guide 620, the tube 630, and the fiber optic tube 640 may be coaxial with one another.

The light source 650 may be any type of light source configured to produce light and transmit the light to the fiber optic cables 648. In some embodiments, the light source 650 may be a laser light source, although other types of devices for producing light may be used.

In certain embodiments, the assembly 600 may be used as a part of the delivery device 200 described above. In such embodiments, the light source 650 may be positioned within the housing 210 and in communication with the second actuator 218 for activating and deactivating the light source 650. The proximal end 644 of the fiber optic tube 640 may be positioned within the housing 210, while the distal end 642 thereof may be positioned outside of the housing 210. The tube 630 may be fixed to the housing 210, with the proximal end 634 of the tube 630 positioned within the housing 210 and the distal end 632 thereof positioned outside of the housing 210. The tube 630 may be configured for driving the intraocular stent through ocular tissue during use of the delivery device 200, as described above. The guide 620 may be movably attached to the housing 210 and configured to translate relative to the housing 210 between an extended position and a retracted position, similar to the guide 220 described above. Further, a portion of the guide 620 may be attached to, either directly or indirectly, or otherwise in mechanical communication with the first actuator 216 for translating the guide 620 between the extended position and the retracted position for controlling release of an intraocular stent from the delivery device 200.

Figures 6A, 6B, 6C:
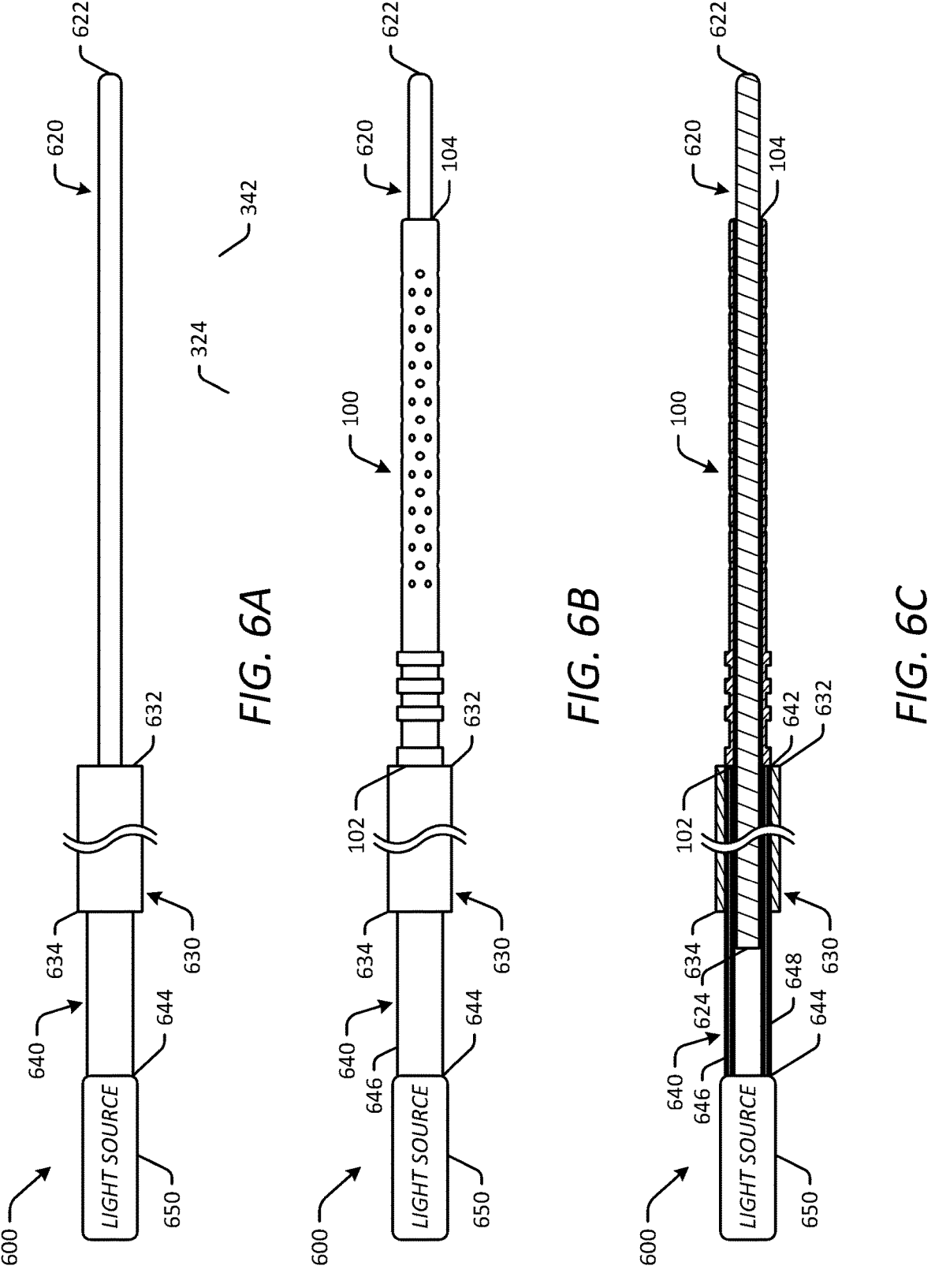
FIG. 6A is a side view of a portion of a delivery device for implanting an intraocular stent in accordance with one or more embodiments of the disclosure, as may be used with the delivery device of FIG. 2A.
FIG. 6B is a side view of the portion of the delivery device of FIG. 6A, with the intraocular stent of FIG. 1A mounted thereto for implantation.
FIG. 6C is a partial cross-sectional side view of the portion of the delivery device of FIG. 6A and the intraocular stent of FIG. 1A.
Figures 6D, 6E:
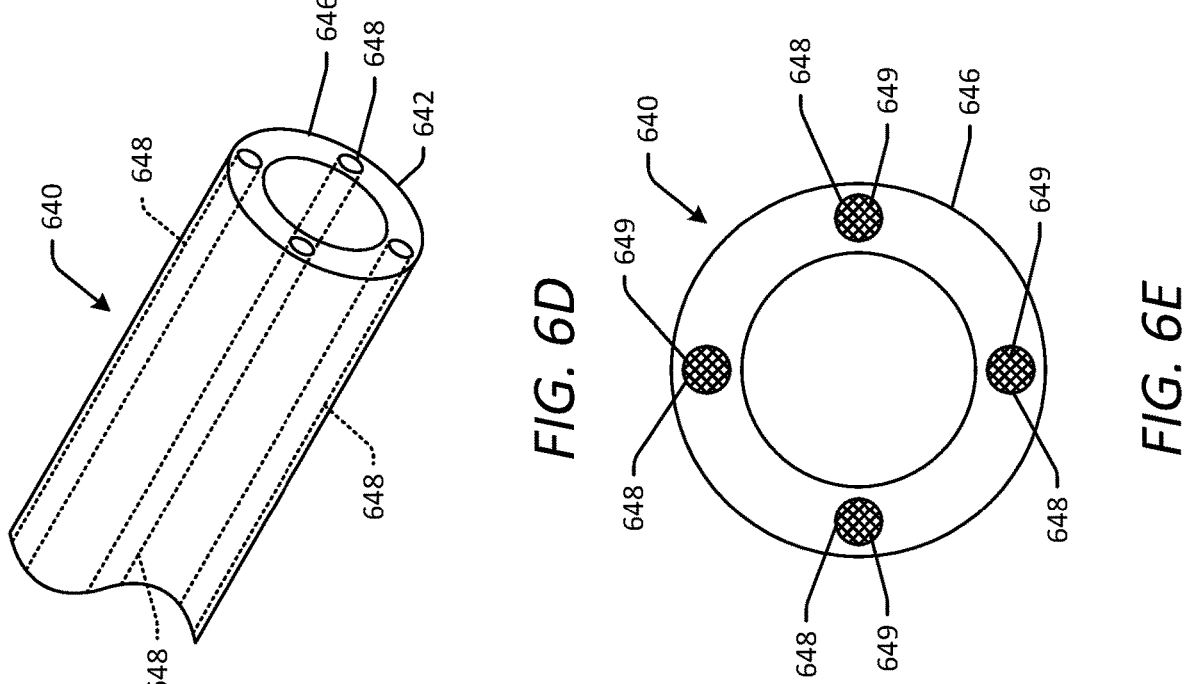
FIG. 6D is a detailed perspective view of a fiber optic tube of the portion of the delivery device of FIG. 6A.
FIG. 6E is a detailed end view of the fiber optic tube of the portion of the delivery device of FIG. 6A.

FIGS. 6B and 6C illustrate the assembly 600 with the intraocular stent 100 mounted thereto. As shown, the stent 100 may be positioned over a portion of the guide 620 such that the guide 620 extends through the central lumen 106 of the stent 100 and the distal end 622 of the guide 620 is exposed beyond the distal end 104 of the stent 100. In this manner, the guide 620 may be inserted into a patient's eye and guide advancement of the stent 100 through the ocular tissue. In certain embodiments, a friction fit may be formed between the circumferentially outer surface of the guide 620 and the circumferentially inner surface of the central lumen 106 to facilitate retention of the stent 100 on the delivery device 200. Further, the stent 100 may engage the tube 630 and the fiber optic tube 640 when mounted to the delivery device 200 for implantation. In certain embodiments, as shown, the distal end 632 of the tube 630 and the distal end 642 of the fiber optic tube 640 may abut the proximal end 102 of the stent 100, such that the stent 100 is prevented from moving proximally toward the housing 210 of the device 200. In this manner, the engagement between the tube 630 and the stent 100 may facilitate driving the stent 100 through the ocular tissue to the desired implantation site. In certain embodiments, as shown, the respective longitudinal axes of the guide 620, the tube 630, and the fiber optic tube 640 may be coaxial with one another and coaxial with the longitudinal axis of the stent 100 mounted to the delivery device 200. As described above, once the stent 100 is advanced to the implantation site, such as with the stent 100 positioned between the anterior chamber and the suprachoroidal space, as shown in FIG. 1D, the stent 100 may be released from the delivery device 200. For example, the first actuator 216 may be moved from the first position to the second position, thereby moving the guide 620 from the extended position to the retracted position. Such movement of the guide 620 may remove the guide 620 from the central lumen 106 of the stent 100, while the tube 630 prevents movement of the stent 100 relative to the tube 630 and the housing 210. The stent 100 thus may become disengaged from the delivery device 200, and the device 200 may be removed from the patient.

During the implantation procedure, such as during insertion of the intraocular stent 100 into the patient's eye and movement of the stent 100 toward the desired implantation site, the assembly 600 may be used to illuminate the stent 100. For example, the second actuator 218 may be moved to the on position to activate the light source 650. The light generated by the light source 650 may be delivered to and transmitted by the fiber optic cables 648 of the fiber optic tube 640. The received light may be diffused by the fiber optic cables 648, particularly the textured end regions 649 thereof. In this manner, the light carried by the fiber optic cables 648 may illuminate the stent 100. Ultimately, the illumination of the stent 100 achieved by the assembly 600 may allow the surgeon to easily visualize the stent 100 during the implantation procedure and confidently direct the stent 100 to the desired implantation site.

Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
   an intraocular stent; and
   a stent delivery device, the stent delivery device comprising:
   a guide configured to engage at least a portion of the intraocular stent, the guide having an elongated shape defining a first longitudinal axis; and
   a fiber optic tube configured to engage both the guide and the intraocular stent, the fiber optic tube having an elongated shape defining a second longitudinal axis;
   wherein the first longitudinal axis is coaxial with the second longitudinal axis;
   wherein the guide extends beyond the fiber optic tube to deliver the intraocular stent; and
   wherein, during insertion of the stent delivery device, the fiber optic tube is positioned at a proximal end of the guide opposite a distal tip of the guide, such that the fiber optic tube is not aligned with the distal tip of the guide during insertion.

2. The system of claim 1, wherein at least a portion of the guide is positioned within the fiber optic tube.

3. The system of claim 1, wherein the fiber optic tube comprises:

a tubular casing; and one or more fiber optic cables positioned within a wall thickness of the casing.

4. The system of claim 3, wherein the one or more fiber optic cables comprises a circumferential array of fiber optic cables positioned within the wall thickness of the casing.

5. The system of claim 3, wherein each of the one or more fiber optic cables comprises a textured surface positioned along a distal end thereof.

6. The system of claim 1, further comprising a tube configured to abut a proximal end of the intraocular stent, wherein the tube has an elongated shape defining a third longitudinal axis, and wherein the third longitudinal axis is coaxial with the first longitudinal axis and the second longitudinal axis.

7. The system of claim 6, wherein the guide is configured to translate relative to the tube.

8. The system of claim 3, further comprising a light source in communication with the one or more fiber optic cables and configured to generate light for transmission to the fiber optic cable.

9. The system of claim 1, further comprising a housing, wherein at least a portion of the guide and at least a portion of the fiber optic tube are positioned within the housing.

10. The system of claim 9, wherein the guide is configured to translate relative to the housing.

11. The system of claim 1, wherein the fiber optic tube comprises a central passage defined therein, and wherein at least a portion of the guide is positioned within the central passage.

\* \* \* \* \*